US012295743B2

(12) United States Patent
Cohen et al.

(10) Patent No.: US 12,295,743 B2
(45) Date of Patent: May 13, 2025

(54) QUANTIFICATION OF HEART FAILURE USING MOLECULAR CHEMICAL IMAGING

(71) Applicant: CHEMIMAGE CORPORATION, Pittsburgh, PA (US)

(72) Inventors: Jeffrey K. Cohen, Pittsburgh, PA (US); J. Christopher Post, Mars, PA (US); Shona Stewart, Pittsburgh, PA (US); Patrick J. Treado, Pittsburgh, PA (US); Heather Gomer, Sewickley, PA (US); Aaron Smith, Monroeville, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 374 days.

(21) Appl. No.: 16/781,610

(22) Filed: Feb. 4, 2020

(65) Prior Publication Data
US 2020/0245930 A1 Aug. 6, 2020

Related U.S. Application Data

(60) Provisional application No. 62/800,860, filed on Feb. 4, 2019.

(51) Int. Cl.
*A61B 5/00* (2006.01)
*G01J 3/02* (2006.01)
(Continued)

(52) U.S. Cl.
CPC .......... *A61B 5/4878* (2013.01); *A61B 5/0077* (2013.01); *A61B 5/7425* (2013.01); *G01J 3/0229* (2013.01); *G01J 3/2823* (2013.01); *G01J 3/42* (2013.01); *G01J 2003/2826* (2013.01)

(58) Field of Classification Search
CPC .......... G01J 3/42; A61B 5/0075; A61B 5/441; A61B 5/4878
See application file for complete search history.

(56) References Cited

U.S. PATENT DOCUMENTS 6,332,091 B1 * 12/2001 Burns ................. A61B 5/0059
600/475
6,640,130 B1   10/2003 Freeman et al.
(Continued)

FOREIGN PATENT DOCUMENTS

CN    101744611 A    6/2010
CN    103622674 A    3/2014
(Continued)

OTHER PUBLICATIONS

Morris, Hannah R. et al. "Liquid Crystal Tunable Filter Raman Chemical Imaging". Applied Spectroscopy, vol. 50, No. 6, 1996, pp. 805-811. (Year: 1996).*
(Continued)

*Primary Examiner* — Michael A Lyons
(74) *Attorney, Agent, or Firm* — DLA Piper LLP (US)

(57) ABSTRACT

Systems and methods of detecting and monitoring edema in a subject are described. The systems and methods include light sources, image detectors, filters, and processors that determine whether a subject has edema and the degree of severity. In some embodiments, the processor fuses data from more than one imaging modality.

21 Claims, 9 Drawing Sheets

(51) Int. Cl.
*G01J 3/28* (2006.01)
*G01J 3/42* (2006.01)

(56) References Cited

U.S. PATENT DOCUMENTS

| | | | |
|---|---|---|---|
| 7,577,469 B1 | 8/2009 | Aronowitz et al. | |
| 2001/0052979 A1* | 12/2001 | Treado | G02B 21/365 |
| | | | 356/326 |
| 2002/0193689 A1 | 12/2002 | Bernstein et al. | |
| 2003/0060693 A1 | 3/2003 | Monfre et al. | |
| 2005/0065813 A1 | 3/2005 | Mishelevich et al. | |
| 2006/0247514 A1 | 11/2006 | Panasyuk et al. | |
| 2006/0250613 A1* | 11/2006 | Demuth | G01N 21/658 |
| | | | 356/301 |
| 2008/0081975 A1 | 4/2008 | Agashe et al. | |
| 2008/0192246 A1 | 8/2008 | Neiss et al. | |
| 2008/0298402 A1 | 12/2008 | Rossi et al. | |
| 2009/0082637 A1 | 3/2009 | Galperin | |
| 2010/0100395 A1 | 4/2010 | Prasad et al. | |
| 2010/0106210 A1 | 4/2010 | Hedberg et al. | |
| 2014/0032242 A1 | 1/2014 | LaBorde et al. | |
| 2014/0183366 A1* | 7/2014 | Cole | G01J 5/0803 |
| | | | 438/73 |
| 2014/0231626 A1* | 8/2014 | Nelson | G01J 3/0264 |
| | | | 250/208.1 |
| 2014/0253921 A1 | 9/2014 | Chen | |
| 2014/0268104 A1* | 9/2014 | Treado | G01J 3/44 |
| | | | 356/51 |
| 2014/0323822 A1 | 10/2014 | Addison et al. | |
| 2015/0044098 A1 | 2/2015 | Smart et al. | |
| 2016/0004820 A1 | 1/2016 | Moore | |
| 2016/0042513 A1 | 2/2016 | Yudovsky | |
| 2016/0140316 A1 | 5/2016 | Spiegel et al. | |
| 2016/0370228 A1* | 12/2016 | Tok | G01J 3/433 |
| 2017/0071510 A1* | 3/2017 | Delbeke | A61B 5/1455 |
| 2018/0188516 A1 | 7/2018 | Engelhardt | |
| 2019/0231260 A1 | 8/2019 | Stewart et al. | |

FOREIGN PATENT DOCUMENTS

| | | | |
|---|---|---|---|
| CN | 103622674 B | 3/2015 | |
| CN | 104757949 A | 7/2015 | |
| CN | 108968922 A | 12/2018 | |
| JP | 2009515663 A | 4/2009 | |
| WO | 2007061754 A1 | 5/2007 | |
| WO | WO-2007088382 A1 * | 8/2007 | G01J 3/02 |
| WO | 2018009670 A1 | 1/2019 | |

OTHER PUBLICATIONS

Leitz, C. et al. "Germanium CCDs for large-format SWIR and X-ray imaging". JINST 12 C05014, 2017. (Year: 2017).*

Kosonocky, Walter F. et al. "160×244 Element PtSi Schottky-Barrier IR-CCD Image Sensor". IEEE Transactions on Electron Devices, vol. Ed-32, No. 8, Aug. 1985, pp. 1564-1573. (Year: 1985).*

International Search Report and Written Opinion dated Apr. 23, 2020 for International Application No. PCT/US2020/016589.

Kollias et al. "Optical Non-Invasive Approaches to Diagnosis of Skin Diseases" Dec. 1, 2002, Optical Diagnostics in Dermatology 7(1): pp. 64-75.

Stamatas G.N., et al., "In Vivo Monitoring of Cutaneous Edema Using Spectral Imaging in the Visible and Near Infrared," Journal Of Investigative Dermatology, NL, May 4, 2006, vol. 126, No. 8, pp. 1753-1760, DOI: 10.1038/sj.id.5700329, ISSN 0022-202X, XP055288513.

* cited by examiner

QUANTIFICATION OF HEART FAILURE USING MOLECULAR CHEMICAL IMAGING

CROSS-REFERENCE TO RELATED APPLICATIONS

This application claims priority to U.S. Provisional Patent Application No. 62/800,860 filed on Feb. 4, 2019, the entire contents of which is incorporated by reference.

FIELD

Edema is swelling that is caused by excess fluid trapped in the tissues of the body, and is often accompanied by swelling, tightness, and pain in the affected tissues. Edema is concerning to medical professionals because it is often a symptom of a serious medical condition, including congestive heart failure, liver disease, blood clots, tumors that obstruct the flow of blood or lymph fluid, allergic reactions, low albumin, kidney disease, pregnancy, and adverse reactions to medications. While edema can occur in tissues throughout the body, it is frequently detected in limbs and/or extremities including arms, legs, hands, feet, ankles, and calves. Edema can also be detected in the abdomen or at a location of inflammation, such as during an allergic reaction. Edema can also occur after exercise, as a response to physical exertion, or from a diet high in salt.

Heart failure can result from any structural or functional abnormality that impairs the ability of the ventricle to eject blood (systolic heart failure) or to fill with blood (diastolic heart failure). Prevalence of heart failure increases with patient age, and a study of over 1.3 million heart failure patients reported that 24.8% of patients were readmitted within 30 days of discharge. The above factors combined with the cost of hospitalization means that the ability to predict and prevent heart failure readmissions would be useful for reducing healthcare costs and improving the quality of patient care.

Heart failure is diagnosed based on symptomatology, physical examination, medical and family history and test results, including blood tests and imaging. A common symptom of heart failure is edema, and edema is commonly assessed in a clinical setting by measuring whether and to what degree a patient has pitting edema. Along with other information, a test of pitting edema is used to determine whether a particular patient is suffering from heart failure.

Although it is non-invasive and simple to administer, testing for pitting edema is subjective and requires training. To test for pitting edema, a clinician applies pressure with his or her index finger to the skin of a patient and measures the depth of the indentation and the period of time required for the skin to recover its original shape, i.e., for the indentation to vanish. The location of the test is generally the patient's ankle or mid-tibia, but is selected by the clinician to represent the point of greatest edema. The presence of pitting edema is graded on a scale of 0-4+, which is intended to convey the indentation depth and recovery time. The amount of pressure applied is based on the clinician's training and clinical experience, and while quantitative guidelines exist for the final graded score, in practice the grading is subjective and based on the judgement of the particular clinician.

Testing for edema is useful not only during hospitalization or clinical treatment, but also after patient discharge. For heart failure patients, one common treatment is the prescription of diuretics, which cause the patient to lose body fluids by increasing the production of urine. While this treatment is effective in reducing blood pressure, proper dosing and patient compliance is sometimes difficult, which causes a buildup in fluid and therefore edema. This causes frequent and costly clinical follow-up visits for patient monitoring or even hospital visits if the edema is severe.

Alternative non-invasive edema measurements have been proposed, including measurements of ankle circumference, patient questionnaires, and indirect measurements of leg volume. However, these methods have been difficult to correlate with the classical and well-understood grades of a pitting edema assessment. Invasive implantable devices such as the CardioMEMS™ HF system available from Abbott Laboratories have been proposed to continuously measure blood pressure, but have high costs due to the necessary implantation. There is a need for low-cost, non-invasive devices and methods to monitor patients for signs of edema. Such devices and methods should be useable by persons with limited or no medical training including the subjects themselves, subjects' family members, persons living with the subjects, and caregivers. The devices and methods should also be usable outside of clinical environments, such as in subjects' homes and places of employment.

SUMMARY

The disclosure includes systems for detecting edema in a subject, as well as methods for detecting edema in a subject.

In one embodiment, there is a system for detecting edema in a patient, the system comprising: a light source configured to irradiate a subject's tissue with light; an image detector configured to collect reflected light from the subject's tissue and generate data associated with the reflected light; and a processing device operably connected to the image detector and configured to: receive the data associated with the reflected light, calculate the intensity of the reflected light, and determine whether the subject's tissue exhibits symptoms of edema.

In another embodiment, the processing device is further configured to determine a control measurement for a control sample.

In another embodiment, the processing device is further configured to: compare the calculated intensity of the reflected light against the control measurement; and determine an edema score for the subject, wherein the edema score represents at least one of whether the subject has edema and a severity of the subject's edema.

In another embodiment, the system further comprises at least one filter configured to filter the reflected light.

In another embodiment, the at least one filter is a tunable filter configured to filter the reflected light a specific wavelength range.

In another embodiment, the at least one filter is at least one of a liquid crystal tunable filter (LCTF), a Fabry Perot tunable filter, a multi-conjugate crystal tunable filter, and a conformal filter.

In another embodiment, the system further comprises a plurality of tunable filters.

In another embodiment, the plurality of tunable filters are configured to filter the reflected light to wavelength ranges of at least one of visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wavelength infrared (MWIR), long-wavelength infrared (LWIR), far-infrared (FIR), infrared (IR), and terahertz radiation.

In another embodiment, the light source comprises at least one of incandescent lamp, halogen lamp, light emitting diode (LED), chemical laser, solid state laser, organic light emitting diode (OLED), electroluminescent device, fluorescent light, gas discharge lamp, metal halide lamp, xenon arc lamp, induction lamp, an ambient light source, or any combination of these light sources.

In another embodiment, the image detector comprises at least one of a Si CMOS, Si CCD, Ge CCD, Ge CMOS, InGaAs CCD, InGaAs CMOS, PtSi CCD, PtSi CMOS, HgCdTe CCD, HgCdTe CMOS, InSb CCD, InSb CMOS, CQD CCD, or CQD CMOS.

In another embodiment, the processor is further configured to fuse intensity data from two or more imaging modalities.

In another embodiment, the two or more imaging modalities comprise a visible image, a hyperspectral image, a shortwave infrared hyperspectral image, a medium-wavelength infrared hyperspectral image, a long-wavelength infrared hyperspectral image, and combinations thereof.

In another embodiment, the system further comprises at least one display device operably connected to the processing device and configured to display one or more images received from the processing device, the one or more images representative of the subject's tissue.

In another embodiment, the system further comprises optics for producing a non-imaging spectrograph.

In one embodiment, there is a method for detecting edema in a subject, the method comprising: irradiating, by a light source, a subject's tissue with light; collecting, by an image detector, reflected light from the subject's tissue; generating, by the image detector, data associated with the reflected light; receiving, by a processing device operably connected to the image detector, the reflected light; calculating, by the processing device, the intensity of the reflected light; and determining, by the processing device, whether the subject's tissue exhibits symptoms of edema.

In another embodiment, the method further comprises determining, by the processing device, a control measurement for a control sample.

In another embodiment, the method further comprises: comparing, by the processing device, the calculated intensity of the reflected light against the control measurement; and determining, by the processing device, an edema score for the subject, wherein the edema score represents at least one of whether the subject has edema and a severity of the subject's edema.

In another embodiment, the method further comprises filtering, by at least one filter, the reflected light.

In another embodiment, the at least one filter is a tunable filter configured to filter the reflected light within a specific wavelength range.

In another embodiment, the at least one filter is at least one of a multivariate optical elements (MOE), liquid crystal tunable filters (LCTF), acousto-optic tunable filter (AOTF), multi-conjugate tunable filter (MCF), Fabry Perot angle tuned filters, Lyot filters, Evans split element liquid crystal tunable filters, Solc liquid crystal tunable filters, fixed wavelength Fabry Perot tunable filters, air-tuned Fabry Perot tunable filters, mechanically-tuned Fabry Perot tunable filters, and liquid crystal Fabry Perot tunable filters.

In another embodiment, the method further comprises filtering, by a plurality of filters, the reflected light to wavelength ranges of at least one of visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wavelength infrared (MWIR), long-wavelength infrared (LWIR), far-infrared (FIR), infrared (IR), and terahertz radiation.

In another embodiment, the light source comprises at least one of incandescent lamp, halogen lamp, light emitting diode (LED), chemical laser, solid state laser, organic light emitting diode (OLED), electroluminescent device, fluorescent light, gas discharge lamp, metal halide lamp, xenon arc lamp, induction lamp, and an ambient light source, and combinations of the above.

In another embodiment, the detector comprises at least one of a Si CMOS, Si CCD, Ge CCD, Ge CMOS, InGaAs CCD, InGaAs CMOS, PtSi CCD, PtSi CMOS, HgCdTe CCD, HgCdTe CMOS, InSb CCD, InSb CMOS, CQD CCD, or a CQD CMOS.

In another embodiment, the method further comprises fusing, by the processing device, intensity data from two or more imaging modalities.

In another embodiment, the two or more imaging modalities comprise a visible image, a hyperspectral image, a shortwave infrared hyperspectral image, a medium-wavelength infrared hyperspectral image, a long-wavelength infrared hyperspectral image, and combinations thereof.

In another embodiment, the method further comprises displaying, by at least one display device operably connected to the processing device, one or more images received from the processing device, the one or more images representative of the subject's tissue.

In another embodiment, the method further comprises producing a non-imaging spectrograph.

In one embodiment, there is a method for monitoring edema in a subject, the method comprising: irradiating, by a light source, a subject's tissue with light; collecting, by an image detector, reflected light from the subject's tissue; generating, by the image detector, data associated with the reflected light; receiving, by a processing device operably connected to the image detector, the reflected light; calculating, by the processing device, the intensity of the reflected light; comparing, by the processing device, the intensity of the reflected light to a control measurement to determine a current edema score; and determining a change in an edema level for the subject based upon a comparison of the current edema score and previously collected edema information.

In another embodiment, the method further comprises determining, by the processing device, the previously collected edema information.

In another embodiment, the method further comprises determining, by the processing device, the control measurement for a control sample.

In another embodiment, the method further comprises displaying, by at least one display device operably connected to the processing device, one or more images received from the processing device, the one or more images representative of the subject's tissue.

In another embodiment, the method is performed in at least one of a hospital, nursing home, doctor's office, outpatient facility, office, assisted living facility, a car, bus, train, airplane, ship, workspace, office, mobile home, mobile clinical facility, or personal residence.

BRIEF DESCRIPTION OF THE DRAWINGS

Aspects, features, benefits and advantages of the embodiments described herein will be apparent with regard to the following description, appended claims, and accompanying drawings where:

DETAILED DESCRIPTION

Figure 1:
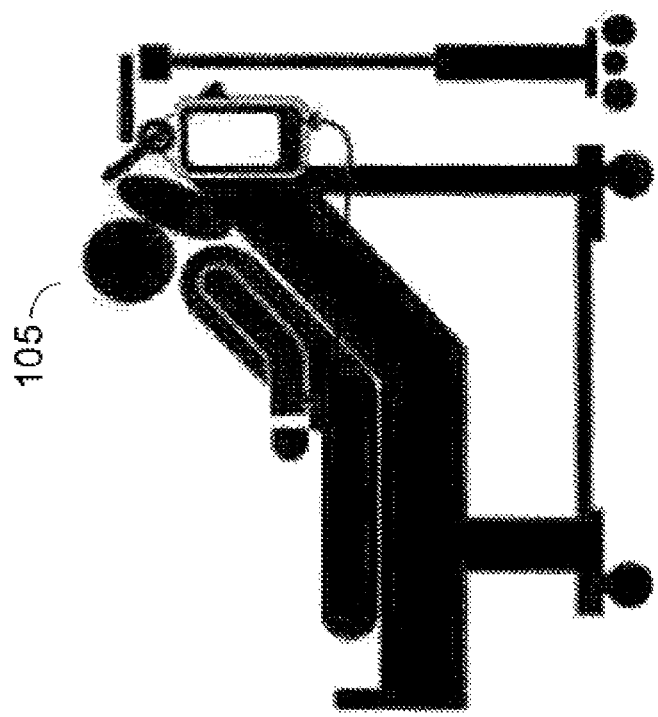
FIG. 1 depicts a sample environment where an imaging system can be used to measure fluid content in a patient's tissue in accordance with one or more embodiments of the present disclosure.
Figure 1:
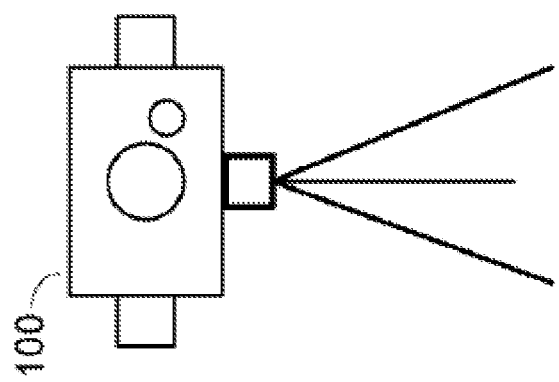

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The present disclosure is directed to systems and methods for detecting edema. More specifically, the present disclosure is directed to systems and methods for the non-invasive detection of edema that offers the potential to aid in ongoing monitoring of a subject's fluid retention, thereby providing clinicians with an objective method of determining edema levels to guide treatment for a variety of disease states.

As used herein, the term "subject" means any human or animal that can be tested or measured for edema. The subject may be healthy, known to have one or more health conditions, or suspected of having one or more health conditions. In some embodiments, the subject is diagnosed with a medical condition or is suspected of having a medical condition; such subjects may alternatively be referred to as a patient.

As used herein, the term "control" means the experimental data that is obtained by collecting reflected light from unaffected areas of a subject. For example, the control can be obtained by collecting reflected light from areas including at least one of the upper arm, thigh, or back. In other embodiments, the term "control" means the experimental data that is obtained by collecting reflected light from a subject that is unaffected by edema, from any tissue location.

In one or more embodiments, a light source illuminates the tissue that is to be analyzed for the presence of edema. The light source is not limited and can be any source that is useful in providing the necessary illumination for the endoscope other ancillary requirements, such as power consumption, emitted spectra, packaging, thermal output, and so forth. In some embodiments, the light source is an incandescent lamp, halogen lamp, light emitting diode (LED), chemical laser, solid state laser, organic light emitting diode (OLED), electroluminescent device, fluorescent light, gas discharge lamp, metal halide lamp, xenon arc lamp, induction lamp, or any combination of these light sources. In some embodiments, the light source is a tunable light source, which means that the light source is monochromatic and can be selected to be within any desired wavelength range. The selected wavelength of the tunable light source is not limited and can be any passband within the visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wavelength infrared (MWIR), long-wavelength infrared (LWIR), far-infrared (FIR), infrared (IR), and terahertz radiation bands. The wavelength ranges are described below.

In some embodiments, the light source is omitted. For example, if the detection of edema is performed outdoors or in other locations with sufficient ambient light, a separate light source is not required and can be omitted. This may be desirable to maximize the portability of the overall system.

In one or more embodiments, an image detector collects incoming photons that are reflected from the tissues of a subject and generates an image for analysis. The functionality and construction of the image detector are not limited. In some embodiments, the image detector is characterized by the wavelengths of light that it is capable of imaging. The wavelengths of light that can be imaged by the image detector are not limited, and include visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wavelength infrared (MWIR), 0054 long-wavelength infrared (LWIR), far-infrared (FIR), infrared (IR), and terahertz radiation. These correspond to wavelengths of about 380 nm to about 720 nm (VIS), about 720 nm to about 1100 nm (NIR), about 400 nm to about 1100 nm (VIS-NIR), about 850 nm to about 1800 nm (SWIR), about 1200 nm to about 2450 nm (eSWIR), about 720 nm to about 2500 nm (NIR-eSWIR), about 3 µm to about 8 µm (MWIR), about 8 µm to about 15 µm (LWIR), about 15 µm to about 1 mm (FIR), about 720 nm to about 1 mm (IR), and about 100 µm to about 1 mm (terahertz). The above ranges may be used alone or in combination of any of the listed ranges. Such combinations include adjacent (contiguous) ranges, overlapping ranges, and ranges that do not overlap. The combination of ranges may be achieved by the inclusion of multiple image detectors, each sensitive to a particular array, or by a single image detector that has a filter array that permits the image detector to sense multiple different ranges.

In some embodiments, the image detector is characterized by the materials from which it is made. The materials of the image detector are not limited and can be selected based on the wavelength ranges that the camera chip is expected to detect. In such embodiments, the camera chip comprises silicon (Si), germanium (Ge), indium gallium arsenide (InGaAs), platinum silicide (PtSi), mercury cadmium telluride (HgCdTe), indium antimonide (InSb), colloidal quantum dots (CQD), or any combination thereof.

In some embodiments, the image detector is characterized by its electrical structure. The electrical structure of the image detector is not limited and can be selected from a charge coupled device (CCD) or a complementary metal oxide semiconductor (CMOS) image sensor. It should be noted that the materials listed above can each be used with either electrical structure to form the final image detector. Examples include Si CMOS, Si CCD, Ge CCD, Ge CMOS, InGaAs CCD, InGaAs CMOS, PtSi CCD, PtSi CMOS, HgCdTe CCD, HgCdTe CMOS, InSb CCD, InSb CMOS, CQD CCD, and CQD CMOS. These image detector structures may be used alone or in combination, either in the same physical image sensor or in multiple separate image sensors.

In some embodiments, the methods and related processes for detecting edema as described herein include illuminating the tissue of a subject with one or more of visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wavelength infrared (MWIR), long-wavelength infrared (LWIR), far-infrared (FIR), infrared (IR), and terahertz radiation. When the above light is reflected from the tissue that is being illuminated, the intensity of the reflected light is compared to a control such as normal tissue or a baseline intensity for normal tissue. In some examples, edema can be detected based on an increase in absorbed light at these wavelengths compared to a subject's control measurements. In some embodiments, systems for detecting edema as described herein include a light source, an image detector, and a processor. The processor is configured to compare the intensity of the reflected light with the expected intensity of the control, such as normal tissue or a baseline intensity of normal tissue.

In some examples, the method may further include processing calculated light intensity data. For example, in some embodiments, the method may include the steps of fusing intensity data from two or more imaging modalities such as, for example, a visible image, a hyperspectral image, a shortwave infrared (SWIR) hyperspectral image, a medium-wavelength infrared (MWIR) hyperspectral image, a long-wavelength infrared (LWIR) hyperspectral image, and the like and combinations thereof. Such fusing can be accomplished by applying a fusion algorithm as is known in the art.

In some embodiments, the systems and methods of the disclosure are configured to generate images of the tissue being analyzed, and the images are used to determine whether the subject has edema. Such images may be formed using any of the spectra listed above and are detected by the appropriate image detector and optics, the spectra including at least one of visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wavelength infrared (MWIR), long-wavelength infrared (LWIR), far-infrared (FIR), infrared (IR), terahertz radiation, and combinations of these. In other embodiments, the systems and methods of the disclosure are configured not to generate images, i.e., they are non-imaging spectroscopy system and methods. In such embodiments, no recognizable image of the tissue is generated, but instead an image is generated based on the compositional and structural signature of the tissue. As above, the spectra for generating the non-imaging spectroscopy data is not limited and includes at least one of visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wavelength infrared (MWIR), long-wavelength infrared (LWIR), far-infrared (FIR), infrared (IR), terahertz radiation, and combinations of these. In some embodiments, the non-imaging spectroscopy or non-imaging spectrograph is at least one of a Raman spectrograph, a SWIR spectrograph, a NIR spectrograph, or a combination of those. In some embodiments, there are additional optics that are configured to produce a non-imaging spectrograph, the non-imaging spectrograph including at least one of a Raman spectrograph, a SWIR spectrograph, a NIR spectrograph, or a combination of those.

In some embodiments, the image detector is used in conjunction with a filter that modifies the light that is to be detected by the image detector. The filter is not limited and is selected from multivariate optical elements (MOE), liquid crystal tunable filters (LCTF), acousto-optic tunable filter (AOTF), multi-conjugate tunable filter (MCF), Fabry Perot angle tuned filters, Lyot filters, Evans split element liquid crystal tunable filters, Solc liquid crystal tunable filters, fixed wavelength Fabry Perot tunable filters, air-tuned Fabry Perot tunable filters, mechanically-tuned Fabry Perot tunable filters, and liquid crystal Fabry Perot tunable filters.

In some embodiments, the use of a conformal filter may improve discrimination performance by, for example, discriminating between a target and background and increasing the throughput of a tunable filter. Increased throughput of the filter improves the speed of the analysis. Exemplary tunable filters that are usable to construct a conformal filter include liquid crystal tunable filters (LCTF), acoustic optical tunable filters (AOTF), Lyot liquid crystal tunable filters, Evans Split-Element liquid crystal tunable filters, Solc liquid crystal tunable filters, ferroelectric liquid crystal tunable filters, Fabry Perot liquid crystal tunable filters, and combinations thereof.

Referring now to the Figures, FIG. 1 illustrates a sample environment where a subject may be tested for edema. For example, as shown in FIG. 1, an imaging and processing device 100 can be positioned adjacent to, for example, a subject 105 lying in a hospital bed. It should be noted the imaging and processing device 100 is shown as being mounted on a tripod by way of example only. In certain implementations, the imaging and processing device 100 can be a handheld device carried by, for example, a doctor, a nurse, a medical technician, a family member, the subject, or any other caregiver or person. In other embodiments, the imaging and processing device 100 can be mounted on a rolling cart or other similar easily movable structure for moving throughout, for example, a hospital, nursing home, doctor's office, outpatient facility, office, assisted living facility, and/or any other location where subjects are present.

The position of the imaging and processing device 100 relative to the subject 105 is based on various factors such as the illumination and image capture characteristics of the imaging and processing device 100. For example, in certain implementations, the imaging and processing device 100 is placed less than about one meter from the subject 105. In another example, the imaging and processing device 100 is placed between about 1 meter and about 2 meters from the subject. In some embodiments, the imaging and processing device 100 is placed more than about 2 meters from the subject. The distance between the imaging and processing device 100 and the subject 105 is not limited and may be determined based on the required amount of reflected light or the required signal quality for accurately processing and determining whether the subject has edema. In some embodiments, the distance between the imaging and processing device 100 and the subject 105 is determined based on the physical dimensions available for the data to be collected, such as the limited space available in a car, bus, train, airplane, ship, workspace, office, mobile home, mobile clinical facility, or personal residence.

Figure 2:
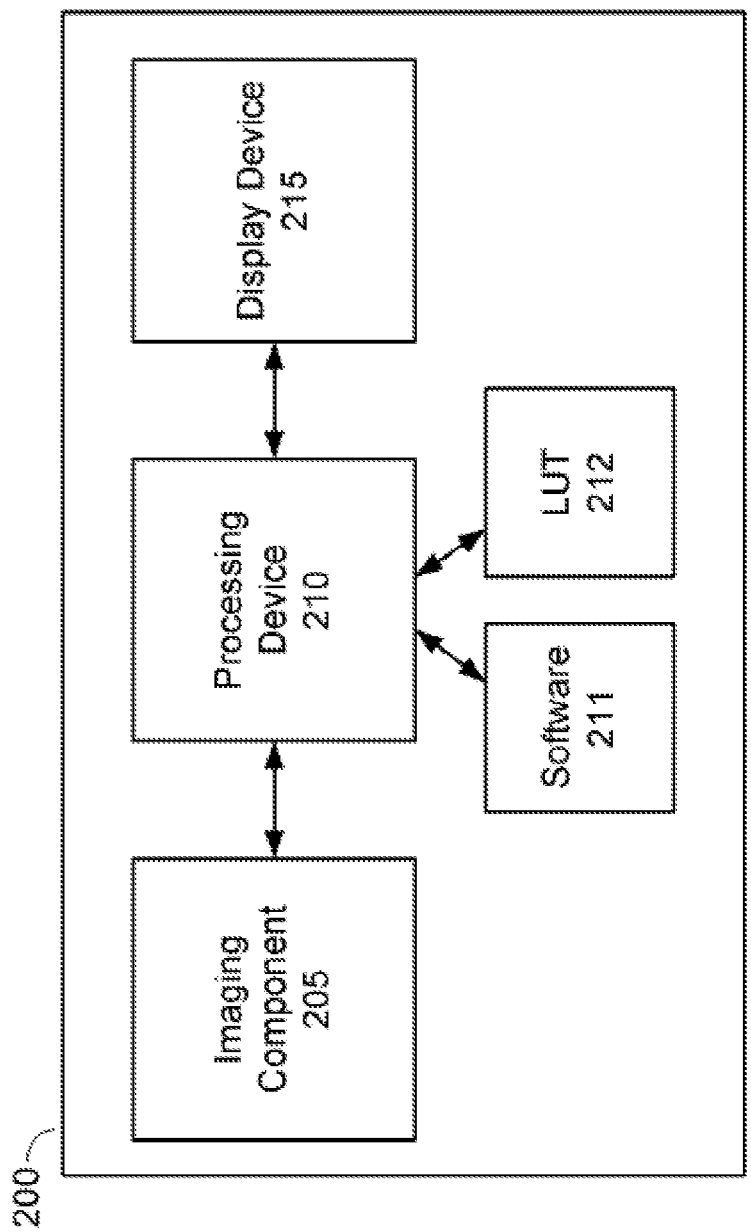
FIG. 2 depicts an illustrative imaging and processing system in accordance with one or more embodiments of the present disclosure.

FIG. 2 illustrates a sample imaging and processing system 200. In certain embodiments, the imaging and processing system 200 can be incorporated into similar environments as the imaging and processing device 100 described above. As shown in FIG. 2, the imaging and processing system 200 can include various components and/or subsystems. For example, in certain implementations, the imaging and processing system 200 can include an imaging component 205 and a processing device 210. In some embodiments, the imaging and processing system 200 can further include a display device 215 operably connected to the processing device 210 and configured to display images and other information related to the detection of edema in a subject.

In certain implementations, the imaging component 205 can include an image detector or other similar imaging device configured to capture the spectral ranges described above. In some embodiments, the image detector includes a VIS image detector and a SWIR image detector. In addition to the image detector, the imaging component 205 may include conformal or other filters that are configured to modify the light that is to be detected by the image detector. The image detector output the collected light into a corresponding electrical signal representing data related to the collected light. The imaging component is described in greater detail in the discussion of FIG. 3 below.

As shown in FIG. 2, the imaging component 205 can be operably connected to the processing device 210. In certain implementations, the processing device 210 can be configured to receive the data relating to the collected reflected light, calculate an intensity of the reflected light, and compare the intensity of the reflected light to a control. Additionally, in various embodiments, the processing device 210 can be operably connected to the display device 215 or to another output device such as, for example, a printer, a router, a computer, a laptop, a monitor, a television, a mobile phone, a smartwatch, or a combination thereof.

In certain implementations, the processing device 210 can be configured to produce one or more images from the data received by the imaging component 205. The one or more images can be displayed, for example, on the display device 215. In some embodiments, the processing device 210 can generate a single image that is displayed on the display device 215. In alternate embodiments, the processing device 210 can generate multiple images based on the data acquired from the imaging component 205.

In some embodiments, the processing device 210 includes a fast switching mechanism to switch between two views (or spectral images) corresponding to spectral data collected by the imaging component 205 from two or more filters. For example, as is discussed in additional detail below in reference to FIG. 3, the imaging component can include one or more tunable filters configured to filter the collected light into wavelength bands. Thus, when a single image is displayed, the image may be generated from spectral data obtained from one filter or the spectral data from multiple filters may be combined or overlaid into a single image, which may provide increased contrast or intensity, thereby providing a comparison of the overlaid images. In other embodiments, separate images corresponding with the data obtained from each filter may be displayed side-by-side.

In some embodiments, the processing device 210 is in communication with one or more non-transitory, computer readable storage mediums. For example, the processing device 210 may be configured to access various software 211 configured to provide instructions to the processing device from a first computer readable storage medium. The instructions, when executed, can cause the processing device 210 to perform various functions, such as the edema detection processes described herein.

The processing device 210 may further be configured to access a computer readable medium that contains a look-up table 212 ("LUT"). In certain implementations, the LUT 212 can include information that, when accessed by the processing device 210, enables the processing device to tune the one or more filters of the imaging component 205 to detect edema in certain tissue. For example, the LUT 212 may include a number of voltages that, when applied to a filter, enable the filter to produce filtered light of a spectral shape associated with one or more tissue types related to various degrees of edema. In the case of a multi-stage filter, the LUT 212 can include voltages that can be applied to each stage of the filter in order to produce filtered light associated with tissue types related to various degrees of edema.

In certain implementations, the processing device 210 can be configured to acquire the appropriate information from the LUT 212 based on user input or image processing. The processing device 210 can then communicate this information to a controller of the imaging component 205, which in turn applies the appropriate voltages to each filter or each stage in each filter. In some embodiments, this process may occur in real time or in near real time providing flexibility for detecting multiple tissue types of interest in near real time. This may allow the user to modify or completely change the displayed image while the intraoperative optical diagnostic device is in use.

It should be noted that, while the software 211 and LUT 212 are shown as being in separate computer readable mediums, this is provided by way of example only. Depending upon the resources available and the design of the imaging and processing system 200, the software 211 and LUT 212 can be implemented on a single computer readable medium. However, in certain implementations, the LUT 212 can be stored at a remote location accessible to the imaging and processing system 200 via, for example, a wired or wireless network communications. In such an arrangement, the LUT 212 can be updated at a central location (for example, a server operated by a manufacturer of the imaging and processing system 200) accessible by a plurality of imaging and processing systems.

Figure 3:
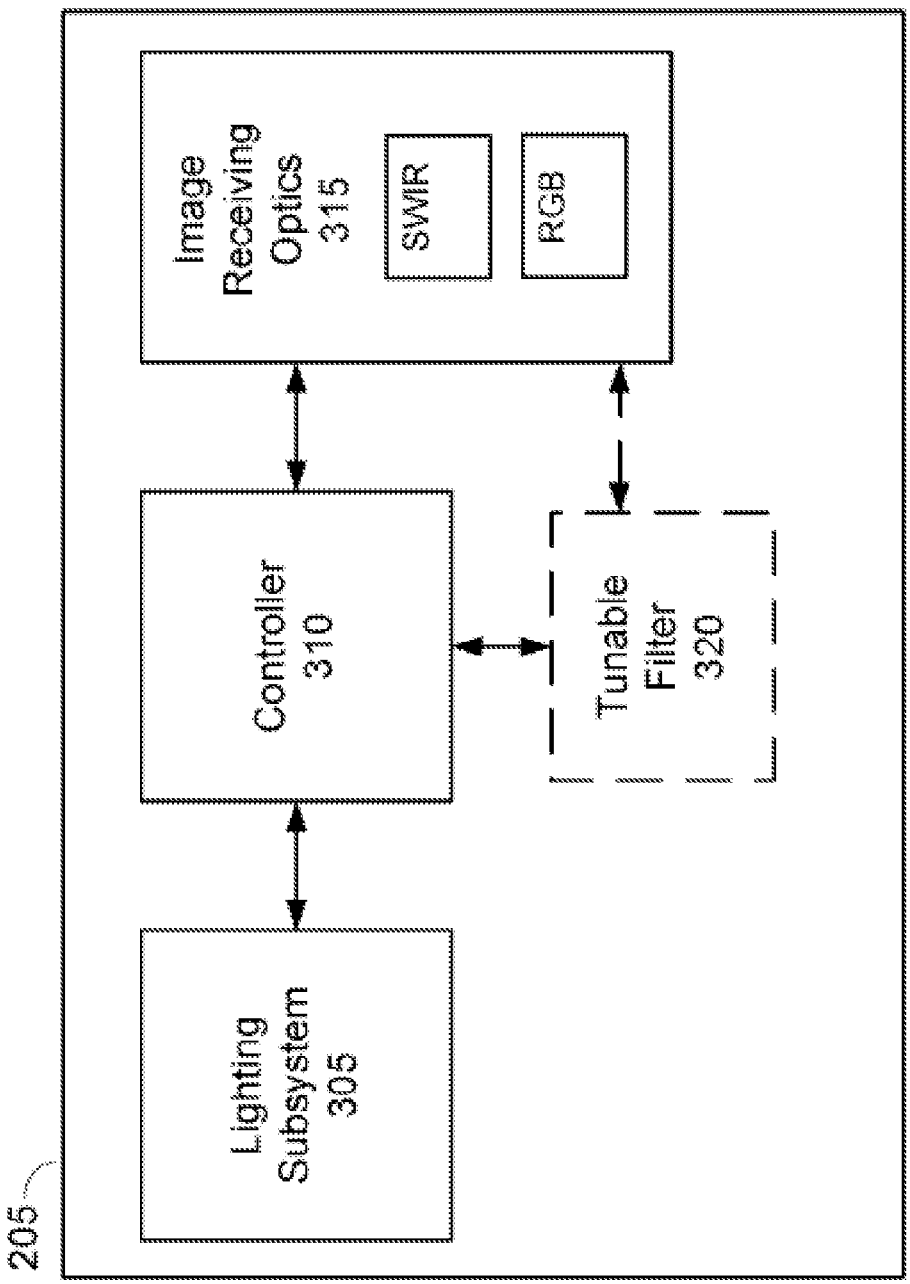
FIG. 3 depicts an illustrative imaging device in accordance with one or more embodiments of the present disclosure.

FIG. 3 illustrates a sample architecture for the imaging component 205 as described above in FIG. 2. As shown in FIG. 3, the imaging component 205 can include various additional components and subsystems. For example, the imaging component 205 can include a controller 310 operably connected to, and configured to control, a lighting subsystem 305, imaging receiving optics 315, and a filter 320. It should be noted that, as shown in FIG. 3, the filter 320 is shown as an optional component. As described below in additional detail, depending upon the implementation of the imaging component 205 and the functionality of its various components, the functionality of the filter 320 can be incorporated into an additional component such as, for example, the image receiving optics 315.

Referring again to FIG. 3, the controller 310 can be implemented as a processing device configured to execute a set of instructions related to operation of the imaging component 205. The instructions can be stored on a computer readable medium (not shown in FIG. 3) operably connected to the controller 310. In certain implementations, the controller 310 can be a dedicated processing device programmed specifically for controlling the various components of the imaging component 205. In such an arrangement, the instructions related to operating the controller 310 can be included on a computer-readable medium integrated directly into the controller 310.

In some embodiments, the lighting subsystem 305 can include filters on one or more light sources. The filters on the one or more light sources are discussed above. For example, in certain embodiments, an infrared (IR) long pass filter is included on a light source to eliminate visible light emitted from the light source. The resultant IR light is eye-safe and invisible to common digital cameras.

In some embodiments, the image receiving optics 315 can be configured to collect light reflected by the irradiated tissue. In some embodiments, the image receiving optics include an image detector such as, for example, a Si CMOS sensor configured to detect VIS RGB information and a CMOS InGaAs sensor configured to detect SWIR information. In alternative embodiments, the image receiving optics 315 include a Si CMOS or CCD image detector which can be used to collect the VIS spectrum or the VIS-NIR spectrum if no infrared cut-off filter is employed over the image detector. In still further embodiments, the image receiving optics 315 may be configured for Raman spectroscopy.

In some embodiments, additional NIR and SWIR cameras and/or detectors can be incorporated into the image receiving optics 315. For example, the image receiving optics 315 can further include a mercury cadmium telluride (HgCdTe) IR detector, an Indium Antimonide (InSb) IR detector or photodiode, a colloidal quantum dot camera, and/or other similar NIR and SWIR cameras and detectors.

In certain embodiments, the imaging receiving optics 315 include optics for focusing light collected from the tissue. For example, in some embodiments, the imaging receiving optics 315 include telescopic or other similar focusing optics configured for at least one of locating and focusing on tissue and/or collecting light from the tissue.

As noted above, in some embodiments, the imaging component 205 includes a filter 320 configured to filter collected light information received by the image receiving optics 315. In certain implementations, the filter 320 can include any tunable filter known in the art including, but not limited to, SWIR multi-conjugate liquid crystal tunable filters, SWIR liquid crystal tunable filters, Fabry Perot angle tuned filters, acousto-optic tunable filters, liquid crystal tunable filters, Lyot filters, Evans split element liquid crystal tunable filters, Solc liquid crystal tunable filters, fixed wavelength Fabry Perot tunable filters, air-tuned Fabry Perot tunable filters, mechanically-tuned Fabry Perot tunable filters, or liquid crystal Fabry Perot tunable filters. In certain embodiments, the filter 320 can be a multi-conjugate liquid crystal tunable filter (MCF). A MCF includes a series of stages composed of polarizers, retarders, and liquid crystals. As a result of this arrangement, the MCF is capable of providing diffraction-limited spatial resolution and spectral resolution consistent with a single-stage dispersive monochromator. The MCF may be tuned to any wavelength in the given filter range. In some embodiments, the MCF may be controlled by a processor. In other embodiments, the filter 320 is a conformal filter that is made of, for example, at least one liquid crystal tunable filter. Similar to the discussion above, in some embodiments, the conformal filter is controlled by a processor.

In certain implementations, the filter 320 can be implemented as a fixed filter array. For example, when processing light collected using a snapshot imaging spectrometer, a fixed filter array can be used to process collected light prior to passing the processed light to the spectrometer for analysis.

In additional embodiments, the filter 320 can be a multivariate optical element filter. In certain embodiments, the filter may be a conformal filter. The term "conformal filter" generally refers to a filter that simultaneously transmits multiple passbands, i.e., spectral shapes. The use of conformal filters can improve discrimination performance by, for example, discriminating between a target and a background and increasing the throughput of a tunable filter, thereby, improving the speed of an analysis. Conformal filters can be tunable to a variety of different configurations. Examples of tunable filters that can be configured for use as a conformal filter include, but are not limited to, a liquid crystal tunable filter, an acoustic optical tunable filter, a Lyot liquid crystal tunable filter, an Evans Split-Element liquid crystal tunable filter, a Solc liquid crystal tunable filter, a ferroelectric liquid crystal tunable filter, a Fabry Perot liquid crystal tunable filter, and combinations thereof.

In additional implementations, the imaging component 205 can be implemented as a dual polarization device. In such an implementation, the imaging component 205 can include an optical separator positioned to receive light reflected from the tissue and separate the reflected light into two or more optical paths. It should be noted that, although such a device can include more than two optical paths, such embodiments are referred to as "dual polarization" devices for simplicity. Each optical path can include one or more filters that reflect light of particular wavelengths removing them from the optical path and allowing other light to pass through the filter to generate filtered light, i.e. a "filtered component." The one or more filters can be any tunable filter or conformal filter, such as those described above. In some embodiments, each optical path can terminate at a detector which is positioned to receive and detect the filtered component. In other embodiments, a single detector may be positioned to simultaneously receive and detect the filtered components from each optical path. Thus, embodiments may include one or more detectors depending on the configuration. The imaging and processing devices of such embodiments, including one or more detectors, may further include a processor electronically connected to the one or more detectors that receive data from each detector. The processor may be configured to analyze the data and generate an image as disclosed herein.

It should be noted that the components included in FIG. 3 and their relative arrangement is provided by way of example only. Depending upon the design and intended functionality of the imaging component 205, the components contained therein and their arrangement may vary accordingly.

Figure 4:
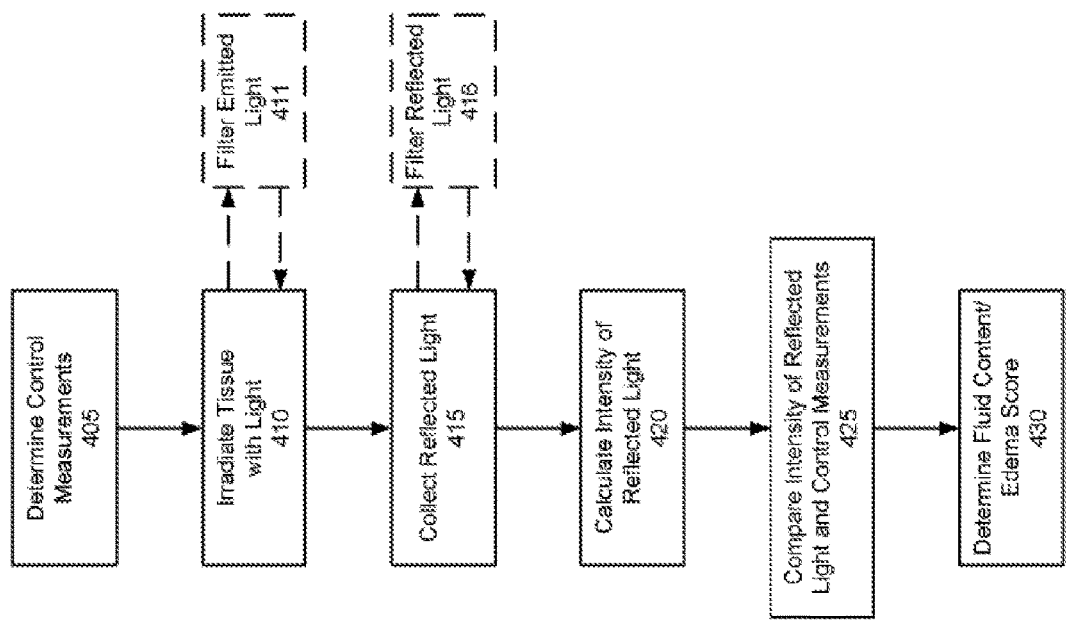
FIG. 4 depicts a sample flowchart illustrating a process for determining a likelihood of a patient having edema in accordance with one or more embodiments of the present disclosure.

FIG. 4 illustrates a sample process for detecting whether a patient is experiencing edema. Initially, a processing device such as processing device 210, can determine 405 control measurements for the subject. For example, as noted above, the control measurements can be determined 405 by collecting reflected light from unaffected tissue of the subject such as, for example, tissue of the upper arm, thigh, or back. Alternatively, control measurements can be determined 405 from an unaffected subject or collection of subjects. For example, in some embodiments, control measurements may be an average absorbance obtained from the arms, legs, hands, feet, ankles, calves, abdomen, or any combination thereof of one or more unaffected subjects.

After control measurements are determined 405, the process can advance to detecting whether the subject is currently exhibiting symptoms of edema. A device, such as imaging and processing device 200 can irradiate 410 the subject's tissue with light. In certain implementations, irradiating 410 the tissue can be carried out using ambient light or a light source such as, for example, a laser illumination source, a broadband light source, or an ambient light source as described above. Depending upon the implementation of the light source, the process can optionally include filtering 411 the emitted light. In some embodiments, the process can include filtering 411 the illuminating light by, for example, removing visible spectrum light.

A detection device, such as the image receiving optics 315, can be configured to collect 415 the light reflected by the subject's tissue. Thus, in various embodiments, collecting 415 the reflected light can be carried out by an image detector such as, for example, the Si CCD detectors or Si CMOS detectors described above, which are typically used to collect visible light for photographs, with Raman spectroscopic imaging systems, and/or with InGaAs or focal plane array (FPA) detectors, which are typically used in near-infrared spectroscopic imaging systems. The particular detection device used to collect 415 the reflected light may be an independent element of a device for carrying out the methods described above. Alternatively, the image detector can be associated with a light source.

Depending upon the conditions under which the reflected light is collected 415 and the intended processing of the collected light, the collected light can optionally be filtered 416. For example, the reflected light can be filtered 416 into one or more wavelength bands to produce hyperspectral images.

A processing device, such as processing device 210, can be configured to receive information related to the collected reflected light and calculate 420 the intensity of the collected reflected light. In certain implementations, the processing device can calculate 420 the intensity of collected reflected light having wavelengths of about 900 nm to about 1300 nm, about 1400 nm to about 1550 nm, or combinations thereof, or any individual wavelength or range encompassed by these ranges. For example, in some embodiments, the processing device may calculate 420 an intensity of reflected light having a wavelength of about 700 nm to about 1100 nm, about 1100 nm to about 1300 nm, about 1200 nm to about 1300 nm, about 1100 nm to about 1250 nm, about 900 nm to about 1100 nm, about 900 nm to about 1150 nm, or combinations of any of the above ranges made by combining the ranges or respective endpoints. In some embodiments, the processor calculates the intensity of light having a reflected wavelength of about 700 nm, about 750 nm, about 800 nm, about 850 nm, about 900 nm, about 950 nm, about 1000 nm, about 1050 nm, about 1100 nm, about 1150 nm, about 1200 nm, about 1250 nm, about 1300 nm, about 1350 nm, about 1400 nm, about 1450 nm, about 1500 nm, about 1550 nm, about 1600 nm, about 1650 nm, about 1700 nm, about 1750 nm, about 1800 nm, about 1850 nm, about 1900 nm, about 1950 nm, about 2000 nm, or any combination or range that is formed by one or more of the above wavelength values.

The processing device can be further configured to compare 425 the intensity of the reflected light to the control measurements. Changes in absorption of light of these wavelengths can be indicative of edema. As such, by comparing 425 the intensity of the reflected light and control measurements, the processing device can determine 430 a fluid content and/or an edema score for the subject. As used herein, an edema score refers to the likelihood that a subject is currently experiencing edema. An edema score may also provide a quantified reading of the severity of the edema. For example, the edema score can be a number ranging from 0.0 to 1.0. A reading of 0.0 can represent the control measurement of the subject's normalized tissue. In certain implementations, a larger value may represent more severe edema. Thus, the process described above in reference to FIG. 4 can be used to identify a disease or condition associated with edema.

Figure 5:
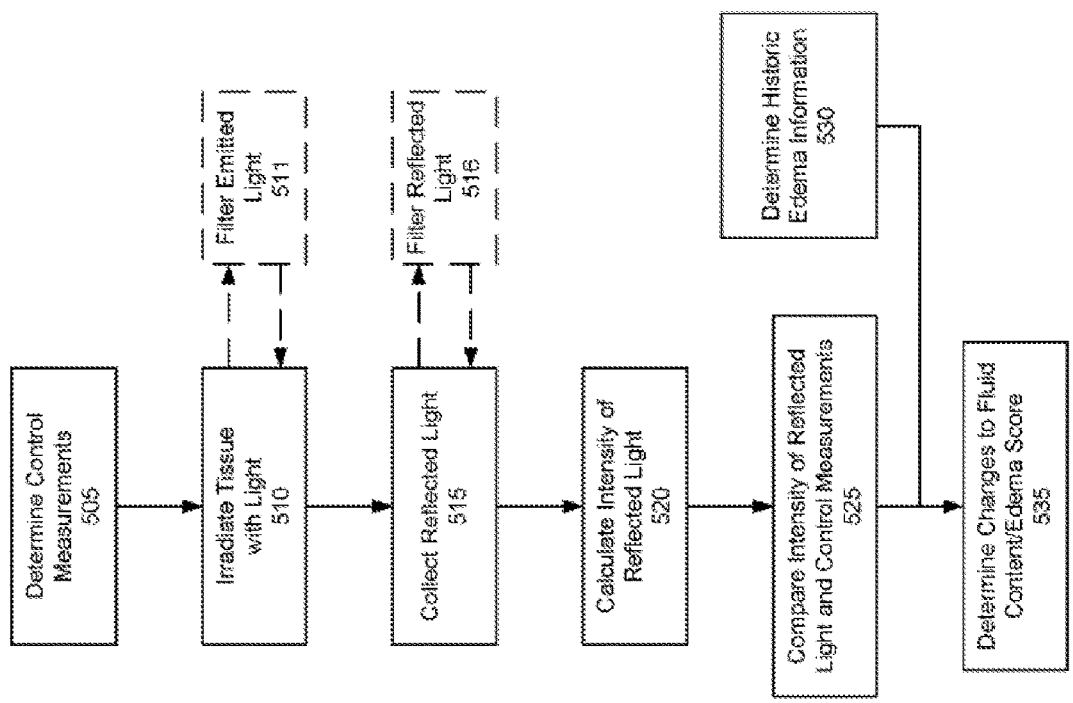
FIG. 5 depicts a sample flowchart illustrating a process for monitoring a patient's edema levels in accordance with one or more embodiments of the present disclosure.

Moreover, the processes and techniques taught herein can further be used to monitor a subject that has been previously identified as having edema. Turning again to the Figures, FIG. 5 illustrates a sample process for detecting and monitoring changes in a subject's edema. Initially, a processing device, such as processing device 210, can determine 505 control measurements for the subject. In some embodiments, the control measurements can be determined 505 by collecting reflected light from unaffected tissue of the subject such as, for example, tissue of the upper arm, thigh, or back. In some embodiments, the control measurements can be determined 505 from an unaffected subject or collection of subjects.

After the control measurements are determined 505, a current edema level or score can be determined for the subject. A device, such as imaging and processing device 200, can irradiate 510 the subject's tissue with light. Depending upon the implementation of the light source, the process can optionally include filtering 511 the emitted light. For example, the process can include filtering 511 the illuminating light by removing VIS light.

A detection device, such as image receiving optics 315, can be configured to collect 515 the light reflected by the subject's tissue. Depending upon the conditions under which the reflected light is collected 515 and the intended processing of the collected light, the collected light can optionally be filtered 516. For example, the reflected light can be filtered 516 into one or more wavelength bands to produce hyperspectral images.

A processing device, such as processing device 210, can be configured to receive information related to the collected reflected light and calculate 520 the intensity of the collected reflected light. The processing device can be further configured to compare 525 the intensity of the collected reflected light to the control measurements to determine a current edema score for the subject.

The processing device can also determine 530 a subject's historic information relating to edema. The historic information can include, for example, data retrieved from the subject's medical record or the like. For example, the subject's edema score as determined in the process described with reference to FIG. 4 can be stored in the subject's medical record. The processing device can then determine 530 the previous edema score from the medical record.

The processing device can compare the current edema score for the subject against the subject's historic edema information to determine 535 whether any changes to the subject's edema level or score have occurred. Such changes can be indicative of changes to the subject's fluid content and/or a changing, worsening, or improving medical condition. A caregiver such as the subject's physician can review the changes in the subject's edema scores or levels and adjust the subject's treatment regimen accordingly.

Figure 6:
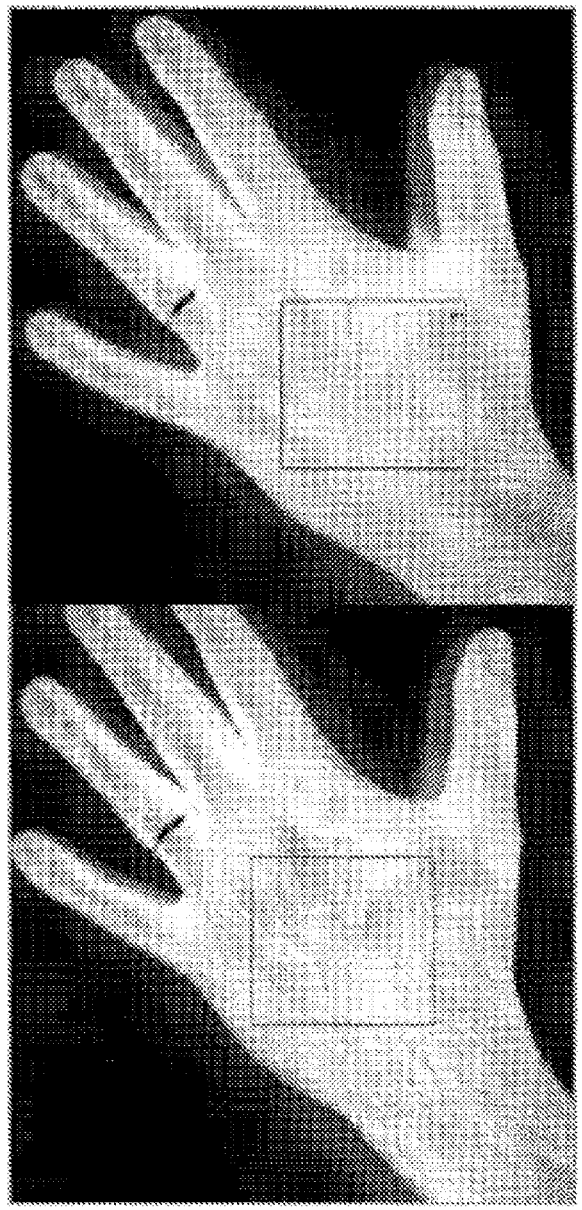
FIG. 6 depicts a sample comparison image of a patient's hand in accordance with one or more embodiments of the present disclosure.
Figure 7:
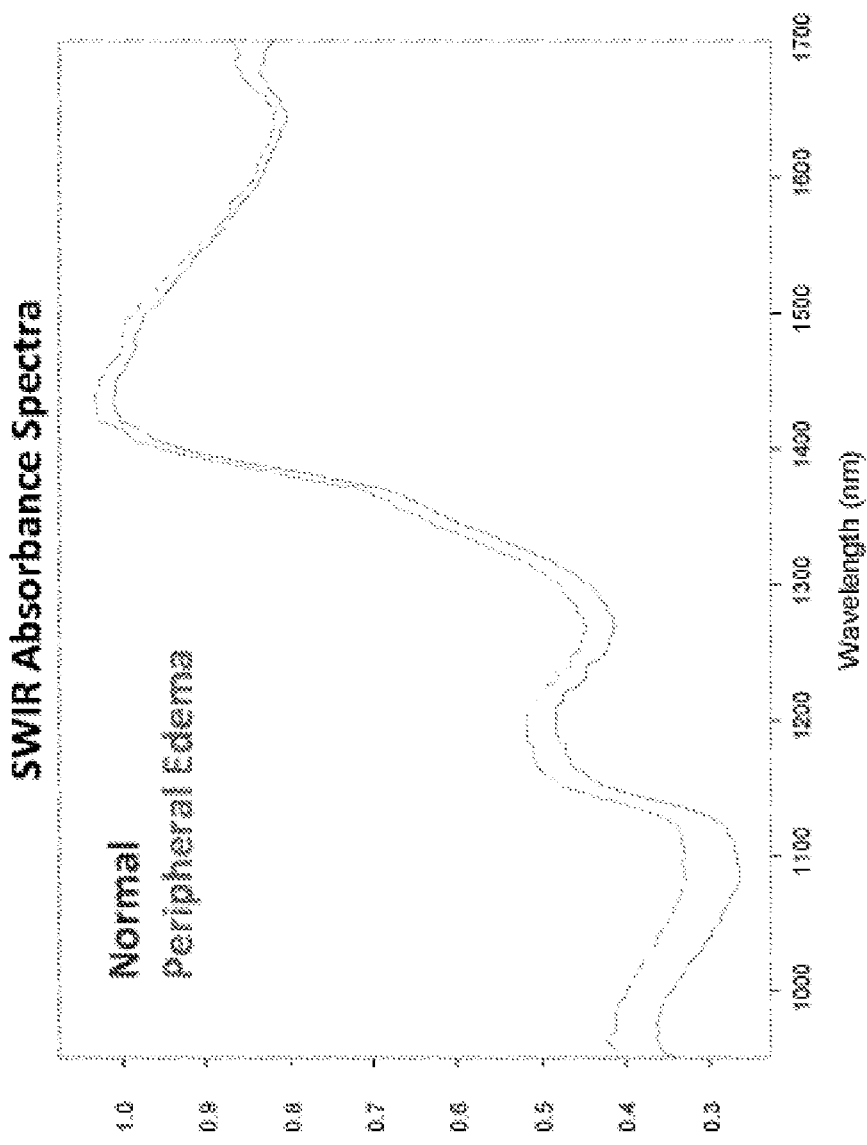
FIG. 7 depicts a sample absorption spectra for a patient's hand in accordance with one or more embodiments of the present disclosure.

FIGS. 6 and 7 illustrate sample output images and data that can be produced for further analysis and/or review using the techniques, systems, and processes as described herein. For example, FIG. 6 illustrates a set of images of a patient's hand. On the left, the image represents normal tissue. In the normal image, the subcutaneous vasculature is highly visible. However, in the right image, the patient is experiencing peripheral edema. Due to the increased water content in the patient's tissue, the vasculature contrast decreases and, as such, the measured calculated intensity of the reflected light will reflect this decrease in vasculature contrast. FIG. 7 illustrates a comparison of the SWIR absorption spectra for normal tissue and tissue exhibiting signs of peripheral edema.

In addition to detecting disease conditions, exercise-related edema can be detected by increased adsorption of light having wavelengths in the range of about 900 nm to about 1300 nm and about 1400 nm to about 1550 nm, when absorption spectra of the hand of an individual pre-workout and post-workout are compared. Accordingly, even mild edema, like exercise-induced edema, can be detected based on the change in intensity of reflected light at these wavelengths. The methods of the embodiments described above are therefore applicable for identifying any condition associated with edema, and not necessarily only those caused by disease or other malady.

It should be noted that the implementation details described above are provided by way of example only. For example, the image acquisition system and environment described in reference to FIG. 1 is provided for illustrative purposes only. Based upon the computation requirements of the processing device and the imaging characteristics of an image capture device, the systems, methods and processes described herein can be incorporated into various devices and systems. For example, systems for detecting edema described and taught herein can be realized using a smartphone having a light source and an image detector. The smart phone may have an installed program or app for calculating the intensity of light at wavelengths in the range of about 900 nm to about 1300 nm and about 1400 nm to about 1550 nm, or any of the ranges defined above. In particular, the program or app may calculate the intensity of collected light at wavelengths of about 700 nm to about 1100 nm. The smartphone can be configured to transmit information related to the calculated intensity of the collected light to a remote location, such as the office of a physician or other similar caregiver. The transmitted information can be used to remotely monitor any changes in the subject's peripheral edema and, if necessary, make treatment changes such as, for example, diet changes, medication changes, exercise recommendations, and other similar changes.

Such systems including smartphones may be particularly useful for detecting edema associated with heart disease and exercise quickly and with a device that a large portion of the population already owns and uses regularly. Rather than teaching a heart failure patient to use a completely new device, or subject the patient to regular testing at a clinician's office, hospital, or other similar location, the patient can learn to use their personal smartphone, or other similar imaging and processing device, to measure their current edema score according to the processes and techniques described herein.

In still further embodiments, the system may be used in various professional and consumer settings. For example, in a professional setting, a system for conformal vision may be incorporated into medical devices that are present in a physician's office, a hospital, a clinic, a retail pharmacy, or other similar healthcare settings. In such professional settings, the system may be used as part of routine testing during a person's recurring visits to such a healthcare setting, although this is but one example of the invention and is not intended to be limiting. The system may alternatively be used in other professional settings, such as beauty salons, hair care salons, spas, nail salons, skin treatment centers, gyms, health clubs, and the like.

The system may also be used in a consumer setting, such as in a person's home, office, or vehicle. This is especially desirable for a system designed to be used by individuals with minimal skill or medical training.

In other examples, the system for detecting edema as described herein can be implemented in, for example, a medical device. In some embodiments, the system may be a spectroscopic imaging device. In such embodiments, spectroscopic imaging may be used to obtain control information from unaffected tissue, such as the upper arm, thigh, or back of the subject and affected or potentially affected tissue at, for example, the foot, ankle, calf, or hand of the subject. In some embodiments, the spectroscopic imaging device may include a tunable filter to filter light into one or more wavelength bands. The bands can then be detected using a spectroscopic imaging device to thereby generate a hyperspectral image. Thus, the method of some embodiments may include separating the reflected light into wavelength bands and generating a hyperspectral image. Such methods may further include overlaying or fusing hyperspectral images and, in some embodiments, overlaying or fusing hyperspectral images with visible images to spatially resolve individual pixels in the hyperspectral image.

EXAMPLES

The following Examples are provided in order to illustrate the invention and are not intended to be limiting. In addition to the components mentioned below, it is contemplated that variations, additions, and omissions are permissible without departing from the scope and spirit of the disclosure.

An apparatus was constructed to analyze edema in subjects. The exemplary apparatus included a high definition VIS (RGB) image detector having 3.1 megapixels resolution and outputting color depth of 8 bits. In addition to the VIS camera, the apparatus also included a SWIR image detector outputting a resolution of 640×512 pixels and incorporating an InGaAs focal plane array. The apparatus also included a multiconjugate filter (MCF) available from ChemImage Corporation of Pittsburgh, PA The apparatus was configured to sense SWIR in the range of about 900 nm to about 1700 nm, utilizing 8 nm bandpass widths. Lighting was provided by several 1000 lux quartz tungsten halogen lamps. The collection optics were a high magnification lens having a 13 mm×10 mm field of view, and a low magnification lens having a field of view of 163 mm×124 mm. The overall weight of the apparatus was 8.3 lbs and 110-120 VAC power was utilized. During operation, tuning increments of 1 nm-20 nm step size acquisitions were used. Furthermore, the detection time for hyperspectral image collection was 50 seconds per collected hypercube. The total amount of time required for a patient was 15 minutes or less. Data was collected and analyzed using ChemImage Spectral Kitchen™ software, available from ChemImage Corporation of Pittsburgh, PA.

An observational study was conducted with 67 human patients. Of the 67 patients, 19 were volunteers that did not have edema, while the remaining 48 had edema in some form. The study endpoints were to discriminate healthy volunteers from edema patients with greater than 0.999 Area Under the Receiver Operating Characteristic (AUROC) curve and to accurately predict pitting edema grades. The majority of the patients were healthy volunteers or edema patients having a grade of 2+ or 3+.

The analysis was performed on the shins of the patients, distinguishing between the right shins and the left shins of the patients, with wavelengths of 1000 nm to 1700 nm. The shin was selected to avoid influence of the tibia. For the first endpoint, discrimination performance of 0.99 AUROC was achieved, satisfying the first experimental endpoint. The data was analyzed using partial least squares discriminant analysis (PLS-DA), which is a statistical method of analysis employed for model creation and data classification. This supervised classification method was used to create a 2-class model discriminating spectra of healthy volunteers and those of heart failure patients exhibiting peripheral edema. As noted above, performance of the model is assessed through a receiver operator characteristic (ROC) curve analysis. A ROC curve is a plot showing sensitivity versus specificity of a test for a binary system. AUROC is a measure that is often used to compare the performance of ROC curves with a single value. The area under a perfect ROC curve is 1.

Another observational study was conducted with 40 human patients. Of the 40 patients, 18 were volunteers that did not have edema, while the remaining 22 has edema in some form. The study endpoints were to discriminate healthy volunteers from edema patients with greater than 0.999 AUROC curve and to accurately detect pitting edema grades. The majority of the patients were healthy volunteers or edema patients having a grade of 2+ or 3+.

This observational study had the same methodology as the observational study that was performed above, but the analysis was performed on the arms of the patients instead of on the shins. Thus, the analysis was performed on the right arms and the left arms of the patients, with wavelengths of 1000 nm to 1700 nm. Discrimination performance of 0.994 AUROC was achieved.

A further observational study was conducted with 42 human patients. Here, the model can include both the shins and forearms simultaneously in the analysis. Of the 42 patients, 18 were volunteers that had no edema, while the remaining 24 had edema in some form. The study endpoints were to discriminate healthy volunteers from edema patients with greater than 0.999 AUROC curve to and to accurately predict pitting edema grades. The majority of the patients were healthy volunteers or edema patients having a grade of 2+ or 3+. The analysis was performed on the shins and forearms of the patients, and discrimination performance of AUROC 0.967 was achieved.

In addition to the 2 class PLS-DA model used to discriminate between healthy patents and those with edema, a 5 class PLS-DA model was generated where 5 models are built with each pitting edema level having its own class to address a secondary endpoint of peripheral edema level prediction. Each shin received a score for each class (0, 1+, 2+, 3+ and 4+) and the highest score became the predicted edema level. An example SWIR output using a 2+ edema patient is demonstrated in FIG. 7. This methodology yielded an accuracy of 84.1% for the tested data set. This result is encouraging given the subjective nature of the ground truth pitting edema test described above. An alternate method to examine the data uses Partial Least Squares Regression to build a model using extracted spectra and the ground truth edema level as the dependent variable. The model was applied to the hypercube of a new patient to produce an edema image that has a higher pixel intensity correlated to higher edema scores; such images generally have higher intensity with a higher ground truth pitting edema level.

Edema is predominantly formed of water, protein, white blood cells, and red blood cells. Discrimination among the populations was explored by comparing average spectra from the healthy and edema populations. Highly discriminating portions of the spectrum were assigned to water (1165 nm, hydroxyl overtone) and lipid and collagen (1220 nm, methine group second overtone). Additional assignments for water, lipid and collagen were documented at 1475-1480 nm. Table 1 below demonstrates spectral peak assignments in the SWIR range. Based on the results, lipid, collagen, and water make up the Basis of Discrimination (BOD) between edema patients having a grade of 3+ and normal subjects (i.e., those having an edema grade of 0).

TABLE 1

| Absorption Peak (nm) | Assignment | Mode |
|---|---|---|
| 1165 | Water | OH Overtone |
| 1220 | Lipid, Collagen | CH str $2^{nd}$ overtone |
| 1475-1480 (collection range 1300-1650 nm) | Water, Collagen, Lipid | OH str $1^{st}$ overtone, $CH_2$ str |

A Cardio Verification Index (CVI) was also constructed using a sample of 42 subjects. The CVI used a regression model with a leave one shin out cross-validation step to predict the edema level. Of the 42 subjects, 18 were control subjects, and 24 had edema. A total of 80 shins were observed of which 36 were normal, 10 were 1+ edema, 14 were 2+ edema, 18 were 3+ edema, and 2 were 4+ edema. The resultant accuracy of the CVI was 85%. It was noted that incorrect edema predictions were generally inaccurate by only one edema grade level, which may indicate discrepancies with the ground truth model rather than the apparatus. It was observed that in partial least squares regression image analysis, there was a general correlation of pixel intensity with edema level for exposed soft tissue.

Testing was also conducted using a 5 class PLS-DA model, with leave one shin out verification utilized. The five classes were normal (0), 1+, 2+, 3+, and 4+ grades of edema. Using the extracted spectra, the overall accuracy was 84.1%, though additional subjects having edema grades of 1+ and 4+ would be required to confirm the results. Table 2 below shows the results of the 5 class PLS-DA model:

|  | Normal | 1+ | 2+ | 3+ | 4+ | Misclass Rate (%) |
|---|---|---|---|---|---|---|
| Normal | 35 | 1 | 1 | 0 | 1 | 7.9 |
| 1+ | 1 | 0 | 2 | 0 | 0 | 100 |
| 2+ | 1 | 0 | 2 | 0 | 0 | 33.3 |
| 3+ | 0 | 0 | 0 | 11 | 0 | 0 |
| 4+ | 1 | 0 | 0 | 0 | 1 | 50 |
| Avg. (%) |  |  |  |  |  | 15.9 |

Figure 8:
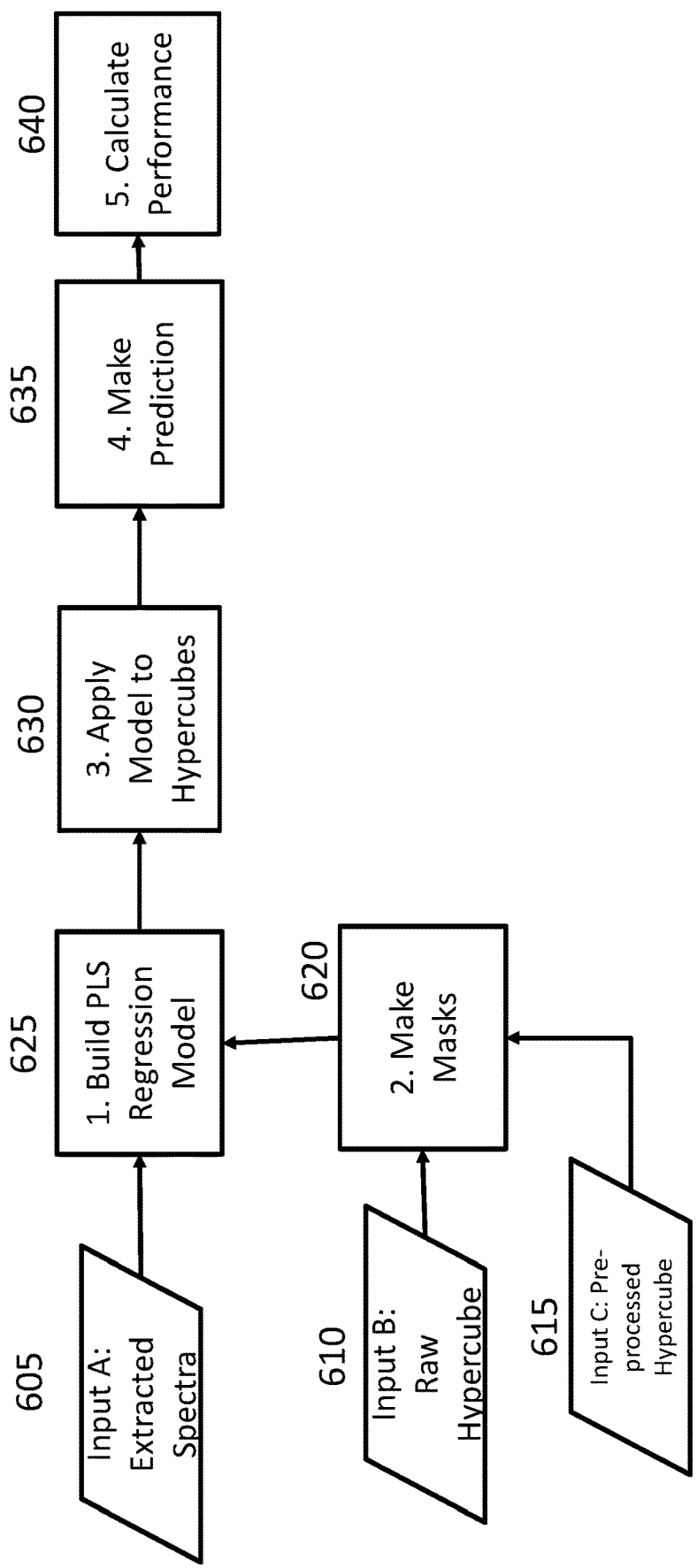
FIG. 8 depicts a flowchart of a partial least squares regression model in accordance with one or more embodiments of the present disclosure.
Figure 9:
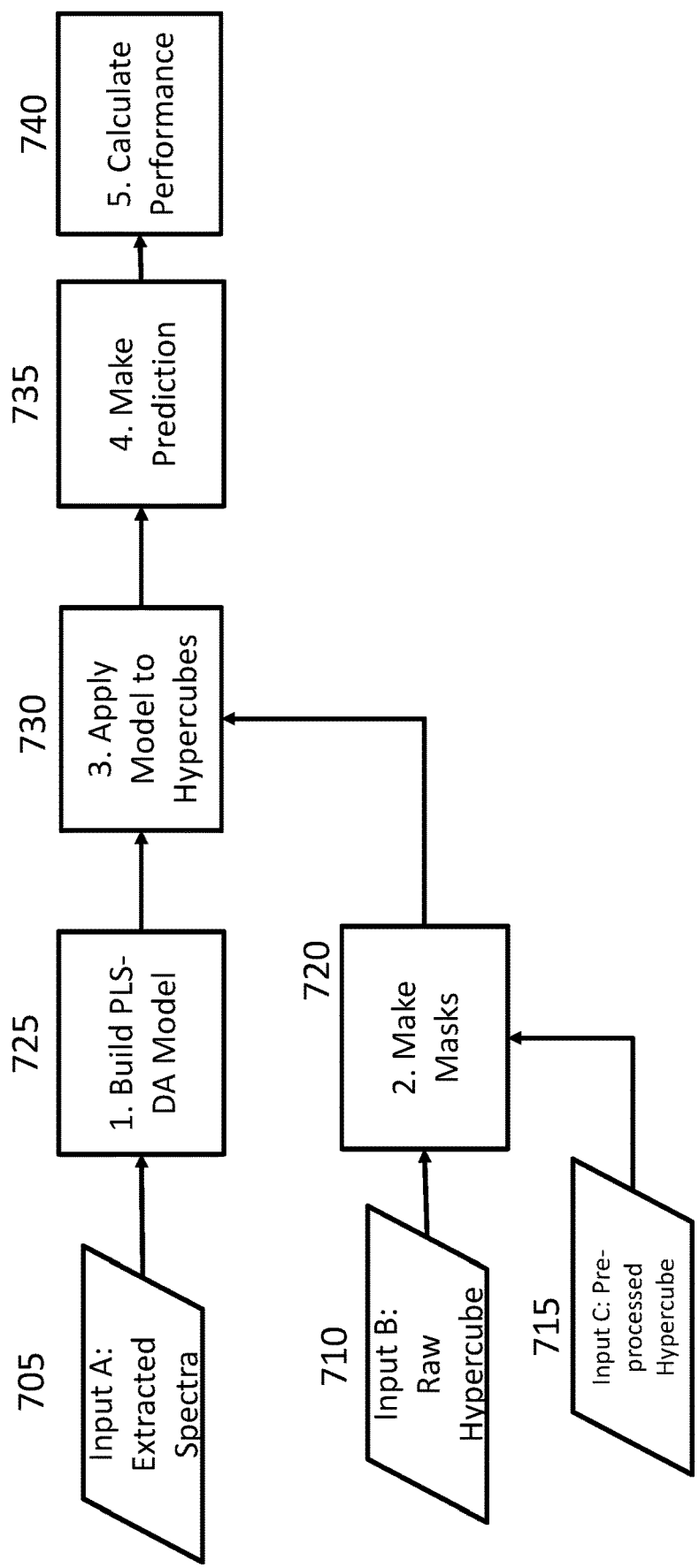
FIG. 9 depicts a flowchart of a partial least squares discriminant analysis model in accordance with one or more embodiments of the present disclosure.

FIGS. 8 and 9 are each depictions of the partial least squares algorithms used in the Examples. In FIG. 8, a partial least squares regression model is depicted, where extracted spectra 605, a raw hypercube 610, and a pre-processed hypercube 615 are input to make masks 620 and thereby build a PLS-R model 625. The model 625 is then applied to hypercubes 630 and utilized to make a prediction 635 and calculate the performance 640 by comparing the predicted edema level with the ground truth edema level. This determines the accuracy of the prediction that is made by the above experimental procedures.

FIG. 9 is similar to FIG. 8 with the exception that a partial least squares discriminant analysis (PLS-DA) is utilized instead. In FIG. 9, extracted spectra 705 are input to build a PLS-DA model 725. A raw hypercube 710 and a pre-processed hypercube 715 are separately input to make masks

720. The PLS-DA model is then applied 730 to the hypercube masks, the results of which are used to make a prediction 735. Finally, the performance is calculated 740 by comparing the predicted edema level with the ground truth level. This determines the accuracy of the prediction that is made by the above experimental procedures.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments

The invention claimed is:

1. A system for detecting edema in a patient, the system comprising:
   a light source configured to irradiate a subject's tissue with light;
   a plurality of tunable filters configured to filter reflected light to wavelength ranges of visible-near infrared (VIS-NIR);
   an image detector configured to collect the filtered reflected light from the subject's tissue and generate data associated with the filtered reflected light; and
   a processing device operably connected to the image detector and configured to:
      receive the data associated with the filtered reflected light, wherein the data comprises at least one hypercube,
      calculate the intensity of the filtered reflected light,
      make hypercube masks using a raw hypercube and a preprocessed hypercube;
      build a partial least squares regression model using the hypercube masks and the data associated with the filtered reflected light; and
      determine whether the subject's tissue exhibits symptoms of edema by applying the partial least squares regression model to the at least one hypercube;
   wherein the image detector comprises at least one of a PtSi charge coupled device (CCD) and a PtSi complementary metal oxide semiconductor (CMOS).

2. The system of claim 1, wherein the processing device is further configured to determine a control measurement for a control sample.

3. The system of claim 2, wherein the processing device is further configured to:
   compare the calculated intensity of the filtered reflected light against the control measurement; and
   determine an edema score for the subject, wherein the edema score represents at least one of whether the subject has edema and a severity of the subject's edema.

4. The system of claim 1, wherein the plurality of tunable filters includes at least one of a liquid crystal tunable filter (LCTF), a Fabry Perot tunable filter, a multi-conjugate crystal tunable filter, and a conformal filter.

5. The system of claim 1, wherein the light source comprises at least one of incandescent lamp, halogen lamp, light emitting diode (LED), chemical laser, solid state laser, organic light emitting diode (OLED), electroluminescent device, fluorescent light, gas discharge lamp, metal halide lamp, xenon arc lamp, induction lamp, an ambient light source, or any combination of these light sources.

6. The system of claim 1, wherein the processing device is further configured to fuse intensity data from two or more imaging modalities.

7. The system of claim 6, wherein the two or more imaging modalities comprise a visible image, a hyperspectral image, a shortwave infrared hyperspectral image, a medium-wavelength infrared hyperspectral image, a long-wavelength infrared hyperspectral image, and combinations thereof.

8. The system of claim 1, further comprising at least one display device operably connected to the processing device and configured to display one or more images received from the processing device, the one or more images representative of the subject's tissue.

9. A method for detecting edema in a subject, the method comprising:
   irradiating, by a light source, a subject's tissue with light;
   collecting, by an image detector, reflected light from the subject's tissue;
   filtering, by a plurality of filters, the reflected light to a wavelength range of visible-near infrared (VIS-NIR);
   generating, by the image detector, data associated with the filtered reflected light, wherein the data comprises at least one hypercube;
   receiving, by a processing device operably connected to the image detector, the filtered reflected light;
   calculating, by the processing device, the intensity of the filtered reflected light;
   making, by the processing device, hypercube masks using a raw hypercube and a preprocessed hypercube;
   building, by the processing device, a partial least squares regression model using the hypercube masks and the data associated with the filtered reflected light;
   determining, by the processing device, whether the subject's tissue exhibits symptoms of edema by using the partial least squares regression model,
   wherein the image detector comprises at least one of a PtSi charge coupled device (CCD) and a PtSi complementary metal oxide semiconductor (CMOS).

10. The method of claim 9, further comprising determining, by the processing device, a control measurement for a control sample.

11. The method of claim 10, further comprising:
    comparing, by the processing device, the calculated intensity of the filtered reflected light against the control measurement; and
    determining, by the processing device, an edema score for the subject, wherein the edema score represents at least one of whether the subject has edema and a severity of the subject's edema.

12. The method of claim 9, wherein the plurality of filters includes at least one of a multivariate optical elements (MOE), liquid crystal tunable filters (LCTF), acousto-optic tunable filter (AOTF), multi-conjugate tunable filter (MCF), Fabry Perot angle tuned filters, Lyot filters, Evans split element liquid crystal tunable filters, Solc liquid crystal tunable filters, fixed wavelength Fabry Perot tunable filters, air-tuned Fabry Perot tunable filters, mechanically-tuned Fabry Perot tunable filters, and liquid crystal Fabry Perot tunable filters.

13. The method of claim 9, wherein the light source comprises at least one of incandescent lamp, halogen lamp, light emitting diode (LED), chemical laser, solid state laser, organic light emitting diode (OLED), electroluminescent device, fluorescent light, gas discharge lamp, metal halide lamp, xenon arc lamp, induction lamp, and an ambient light source, and combinations of the above.

14. The method of claim 9, further comprising fusing, by the processing device, intensity data from two or more imaging modalities.

15. The method of claim 14, wherein the two or more imaging modalities comprise a visible image, a hyperspectral image, a shortwave infrared hyperspectral image, a medium-wavelength infrared hyperspectral image, a long-wavelength infrared hyperspectral image, and combinations thereof.

16. The method of claim 9, further comprising displaying, by at least one display device operably connected to the processing device, one or more images received from the processing device, the one or more images representative of the subject's tissue.

17. A method for monitoring edema in a subject, the method comprising:
- irradiating, by a light source, a subject's tissue with light;
- filtering, by a plurality of filters, reflected light to a wavelength range of visible-near infrared (VIS-NIR);
- collecting, by an image detector, the filtered reflected light from the subject's tissue;
- generating, by the image detector, data associated with the filtered reflected light, wherein the data comprises at least one hypercube;
- receiving, by a processing device operably connected to the image detector, the filtered reflected light;
- calculating, by the processing device, the intensity of the filtered reflected light;
- comparing, by the processing device, the intensity of the filtered reflected light to a control measurement to determine a current edema score;
- making, by the processing device, hypercube masks using a raw hypercube and a preprocessed hypercube;
- building, by the processing device, a partial least squares regression model using the hypercube masks and the data associated with the filtered reflected light; and
- determining a change in an edema level for the subject based upon a comparison of the current edema score and previously collected edema information by using the partial least squares regression model,
- wherein the image detector comprises at least one of a PtSi charge coupled device (CCD) and a PtSi complementary metal oxide semiconductor (CMOS).

18. The method of claim 17, further comprising determining, by the processing device, the previously collected edema information.

19. The method of claim 17, further comprising determining, by the processing device, the control measurement for a control sample.

20. The method of claim 17, further comprising displaying, by at least one display device operably connected to the processing device, one or more images received from the processing device, the one or more images representative of the subject's tissue.

21. The method of claim 17, wherein the method is performed in at least one of a hospital, nursing home, doctor's office, outpatient facility, office, assisted living facility, a car, bus, train, airplane, ship, workspace, office, mobile home, mobile clinical facility, or personal residence.

* * * * *